United States Patent [19]

Varwig et al.

[11] Patent Number: 4,590,016
[45] Date of Patent: May 20, 1986

[54] PREPARATION OF FLUOROMETHYLTHIOBENZOYL FLUORIDES

[75] Inventors: Juergen Varwig, Heidelberg; Gerhard Hamprecht, Weinheim, both of Fed. Rep. of Germany

[73] Assignee: BASF Aktiengesellschaft, Ludwigshafen, Fed. Rep. of Germany

[21] Appl. No.: 589,305

[22] Filed: Mar. 14, 1984

Related U.S. Application Data

[62] Division of Ser. No. 398,424, Jul. 14, 1982, abandoned.

[30] Foreign Application Priority Data

Aug. 1, 1981 [DE] Fed. Rep. of Germany ....... 3130436

[51] Int. Cl.$^4$ .............................................. C07C 51/58
[52] U.S. Cl. ................................................... 260/544 F
[58] Field of Search ...................................... 260/544 F

[56] References Cited

U.S. PATENT DOCUMENTS

| | | | |
|---|---|---|---|
| 2,062,743 | 12/1936 | Daudt et al. ...................... | 260/544 F |
| 2,181,554 | 11/1939 | Kracker et al. .................. | 260/544 F |
| 3,592,861 | 7/1971 | Klauke et al. ...................... | 568/937 |
| 3,801,599 | 4/1974 | Alles ..................................... | 549/365 |

FOREIGN PATENT DOCUMENTS 2117650  10/1972  Fed. Rep. of Germany .

OTHER PUBLICATIONS

Houben-Weyl *Methoden der Org. Chemie,* vol. V/3, p. 122.
*Chem. Ber.,* vol. 112, (1979), pp. 3023-3030.
*J. Am. Chem. Soc.,* vol. 85, (1963), pp. 1314–1318.
*J. Org. Chem.,* vol. 27, (1962), pp. 3164–3168.
*J. Org. Chem.,* vol. 29, (1964), pp. 1–11 and 896–898.
L. Brandsma, J. F. Arens in Saul Patai, "The Chemistry of the Ether Linkage", 1967, pp. 553–565.

*Primary Examiner*—Natalie Trousof
*Assistant Examiner*—L. Hendriksen
*Attorney, Agent, or Firm*—John H. Shurtleff

[57] ABSTRACT

Novel fluoromethylthiobenzoyl fluorides are prepared by reacting a trichloromethylthiobenzoyl chloride with hydrogen fluoride at from 10° to 130° C., and are useful starting materials for the preparation of crop protection agents. The process of the invention is selective in permitting the optional production of either a trifluoromethylthiobenzoyl fluoride or a difluoromonochloromethylthiobenzoyl fluoride, depending upon the temperature employed.

6 Claims, No Drawings

PREPARATION OF FLUOROMETHYLTHIOBENZOYL FLUORIDES

This application is a division of application Ser. No. 398,424, filed July 14, 1982, now abandoned.

The present invention relates to novel fluoromethylthiobenzoyl fluorides and a process for their preparation by reacting a trichloromethylthiobenzoyl chloride with hydrogen fluoride at from 10° to 130° C.

C.A. 49,8172c and French Pat. No. 820,796 have disclosed the preparation of trifluoromethylphenyl sulfides from the corresponding trichloro compounds with the aid of antimony trifluoride or hydrogen fluoride.

Trifluoromethylthio-substituted benzoyl chlorides have hitherto been prepared by an involved method via the aniline derivative, which is prepared from trifluoromethylthionitrobenzene by reduction and is further reacted to give the corresponding benzonitrile and benzoic acid, which is then chlorinated with thionyl chloride (C.A. loc. cit.).

Other methods of obtaining trifluoromethylthiobenzoic acid derivatives, which however still have to be subjected to further reaction steps to obtain the acid chlorides, comprise reacting iodine- or bromine-substituted nitrobenzenes or benzoic acid esters with mercury trifluoromethyl sulfide or copper trifluoromethyl sulfide (U.S. Pat. No. 4,020,169; J. Org. Chem. 41 (1976), 1,644). The mercury compounds required for the reactions are expensive and toxic, and are prepared by an involved method via trichloromethylthiosulfenyl chloride. Copper trifluoromethyl sulfide is synthesized from the mercury compound.

The process disclosed in German Laid-Open Application DOS 2,117,650 gives fluoromethoxybenzoyl fluorides, actually the monofluoro and difluoro compounds, by converting the corresponding trichloromethoxybenzoyl chloride at from 60° to 130° C. under superatmospheric pressure. It is stated that only a reaction at about 130° C. gives a reasonable amount of trifluoro compound. Example 5 shows that a mixture of monofluoro (11.8%), difluoro (79.6%) and trifluoro (5.6%) compounds is obtained at from 29° to 94° C.

We have now found that fluoromethylthiobenzoyl fluorides of the formula

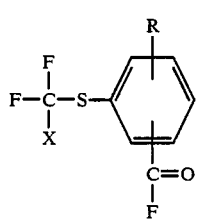

where X is chlorine or fluorine and R is hydrogen, halogen or an aliphatic radical are obtained in an advantageous manner by a process wherein one mole of a trichloromethylthiobenzoyl chloride of the formula

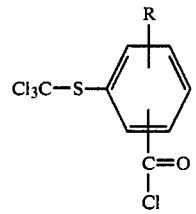

where R has the above meanings, is reacted with from 1.2 to 100 moles of hydrogen fluoride (a) at from 40° to 130° C. and under from 2 to 30 bar for preparation of the trifluoromethylthiobenzoyl fluoride, or (b) at from 10° to 40° C. and under a pressure of from 1 to 10 bar for preparation of the difluoromonochloromethylthiobenzoyl fluoride.

We have also found the novel fluoromethylthiobenzoyl fluorides of the formula

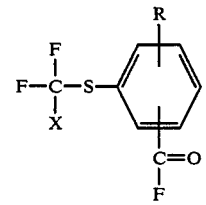

where X is chlorine or fluorine and R is hydrogen, halogen or an aliphatic radical.

If m-trichloromethylthiobenzoyl chloride is used, the reaction can be represented by the following equation:

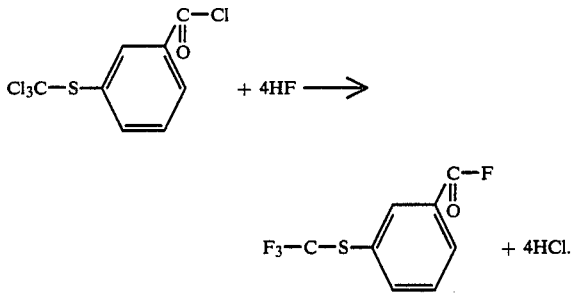

Compared to the prior art, the process according to the invention gives a good yield of the novel fluoromethylthiobenzoyl fluorides in a highly pure form, in a simple and economical manner. All these advantageous properties are surprising since, in the light of German Laid-Open Application DOS 2,117,650, mixtures of all three fluoromethyl compounds and at most a small amount of trifluoro compound would have been expected at the temperatures and pressures according to the invention.

Preferred starting materials II and, accordingly, preferred end products I are those where X is chlorine or fluorine and R is hydrogen, bromine, chlorine or alkyl of 1 to 4 carbon atoms, which radicals can be further substituted by radicals which are inert under the reaction conditions, eg. alkyl or alkoxy of 1 to 4 carbon atoms.

Examples of suitable starting materials II thus include m-trichloromethylthiobenzoyl chlorides and the corresponding benzoyl chlorides which are substituted in the m-, o- or p-position of the phenyl nucleus by bromine, chlorine, methyl, ethyl, propyl, isopropyl, butyl, isobutyl, sec.-butyl or tert.-butyl, and corresponding o- and p-trichloromethyl compounds.

The reaction can be carried out with stoichiometric amounts of the starting compounds or, preferably, with an excess of hydrogen fluoride, advantageously with from 1.2 to 100 moles of HF, preferably from 1.5 to 20 moles of HF, per mole of trichloromethylthiobenzoyl chloride.

The reaction is carried out at from 10° to 130° C., and in particular at from 40° to 130° C., especially from 40° to 80° C., for preparation of the trifluoromethyl compound, and at from 10° to 40° C., especially from 10° to 30° C., for preparation of the difluoromethyl compound, under superatmospheric or atmospheric pressure, continuously or batchwise.

The reaction pressure is from 1 to 30 bar, and in particular from 2 to 30 bar for preparation of the trifluoromethyl compound and from 1 to 10 bar for preparation of the difluoromethyl compound. The HCl gas evolved during the reaction is let off, depending on the desired pressure.

The reaction can be carried out in the presence or absence of a solvent. Examples of suitable solvents are halohydrocarbons, in particular bromo- and chlorohydrocarbons, eg. tetrachloroethylene, 1,1,2,2- and 1,1,1,2-tetrachloroethane, amyl chloride, cyclohexyl chloride, 1,2-dichloropropane, methylene chloride, dichlorobutane, isopropyl bromide, n-propyl bromide, butyl bromide, chloroform, bromoform, ethyl iodide, propyl iodide, chloronaphthalene, dichloronaphthalene, carbon tetrachloride, 1,1,1- and 1,1,2-trichloroethane, trichloroethylene, pentachloroethane, 1,2-dichloroethane, 1,1-dichloroethane, n-propyl chloride, 1,2-cis-dichloroethylene, n-butyl chloride and 2-, 3- and iso-butyl chloride, aliphatic and cycloaliphatic hydrocarbons, eg. pentane, heptane, α-pinene, pinane, nonane, gasoline fractions within a boiling point range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane, and appropriate mixtures. Advantageously, from 80 to 10,000 percent by weight, preferably from 100 to 600 percent by weight, based on starting material II, of the solvent is used.

The reaction can be carried out in the presence or absence of a catalyst such as a compound, eg. a fluoride, of antimony, iron, cobalt, nickel, manganese, titanium, aluminum, boron or chromium.

The reaction can be carried out by stirring hydrogen fluoride and the trichloromethylthiobenzoyl chloride at the reaction temperature for from 0.5 to 10 hours in the presence or absence of a solvent and/or catalyst and removing the resulting hydrogen chloride from the system under a pressure of from 1 to 30 bar. The excess hydrogen fluoride is distilled off and can be recycled. The end product is purified in a conventional manner by distillation. It may also be advantageous to wash the product with water, with or without addition of a water-immiscible solvent.

The fluoromethylthiobenzoyl fluorides which can be obtained by the process according to the invention are useful starting materials for the preparation of crop protection agents. Thus, for example, benzoxazinones having a marked herbicidal action are obtained by reaction with anthranilic acids (German Laid-Open Application DOS 2,914,915).

In the Examples which follow, parts are by weight.

EXAMPLE 1

1,540 parts of m-trichloromethylthiobenzoyl chloride and 1,900 parts of hydrogen fluoride are stirred at 70° C. in a V4A steel autoclave for 6 hours. The pressure is kept at 10 bar by releasing the hydrogen chloride formed. The apparatus is let down, excess hydrogen fluoride is distilled off and the liquid reaction product is distilled. Yield: 891 parts (75% of theory) of m-trifluoromethylthiobenzoyl fluoride of $n_D^{25}$ 1.4777 and boiling point 60° C./5 mbar.

EXAMPLE 2

650 pats of p-trichloromethylthiobenzoyl chloride and 500 parts of hydrogen fluoride are refluxed (20° C.) under atmospheric pressure in a Teflon flask with a reflux condenser for 7 hours. The mixture is worked up and the hydrogen fluoride is distilled off to give 441 parts (83% of theory) of p-chlorodifluoromethylthiobenzoyl fluoride of boiling point 106°–108° C./16 mbar and $n_D^{25}$ 1.5144.

$^{13}$C-NMR (CDCl$_3$) δ (ppm) (TMS as internal standard): $C_1$ 127.22 (D); $C_4$ 135.11 (S); $C_7$ 156.61 (D); $C_2$ 132.25 (S); $C_5$ 136.04 (S); $C_8$ 130.05 (T); $C_3$ 136.04 (S); $C_6$ 132.25 (C).

EXAMPLE 3

2,600 parts of m-trichloromethylthiobenzoyl chloride and 2,000 parts of hydrogen fluoride are stirred under reflux (20° C.) under 1 bar in a Teflon flask with a reflux condenser for 7 hours. The hydrogen fluoride is distilled off to give 1,965 parts (82% of theory) of m-chlorodifluoromethylthiobenzoyl fluoride of boiling point 47°–50° C./0.2 mbar and $n_D^{25}$ 1.5089.

EXAMPLE 4

270 parts of 3-trichloromethylthio-4-chlorobenzoyl chloride and 500 parts of anhydrous hydrogen fluoride are stirred at 70° C. under 20 bar in an autoclave for 8 hours. The product mixture is poured onto ice-water, extracted with methylene chloride and washed with water to give 130 parts (62% of theory) of 3-trifluoromethylthio-4'-chlorobenzoyl fluoride of boiling point 41° C./0.1 mbar.

$^{13}$C-NMR (CdCl$_3$) δ (ppm) (TMS as internal standard): $C_1$ 125.1 (D); $C_4$ 147.9 (S); $C_7$ 115.7 (D); $C_2$ 140.8 (S); $C_5$ 131.9 (S); $C_8$ 129.2 (Q); $C_3$ 126.5 (S); $C_6$ 134.7 (S).

EXAMPLE 5

1,540 parts of p-trichloromethylthiobenzoyl chloride and 1,900 parts of hydrogen fluoride are reacted in a manner similar to that in Example 1 to give a yield of 70% of theory of p-trifluoromethylthiobenzoyl fluoride of boiling point 85°–89° C./16 mbar and $n_D^{25}$ 1.4829.

We claim:

1. A process for the production of a meta- or para-trifluoromethylthiobenzoyl fluoride of the formula

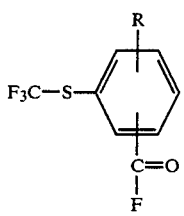

Ia wherein R is hydrogen, bromine, chlorine or alkyl of 1 to 4 carbon atoms, which process comprises:

reacting a trichloromethylthiobenzoyl chloride of the formula

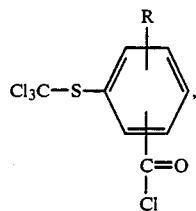

II wherein R has the above meanings, with from 1.2 to 100 moles of hydrogen fluoride per mole of II, at a temperature of from 40° to 130° C. and under a pressure of from 2 to 30 bar.

2. A process for the production of a meta- or para-difluoromonochloromethylthiobenzoyl fluoride of the formula

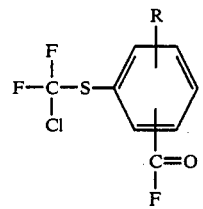

Ib wherein R is hydrogen, bromine, chlorine or alkyl of 1 to 4 carbon atoms, which process comprises:

reacting a trichloromethylthiobenzoyl chloride of the formula

II wherein R has the above meanings, with from 1.2 to 100 moles of hydrogen fluoride per mole of II, at a temperature of from 10° to 40° C. and under a pressure of from 1 to 10 bar.

3. A process as claimed in claim 1, wherein the reaction is carried out with from 1.5 to 20 moles of HF per mole of trichloromethylthiobenzoyl chloride.

4. A process as claimed in claim 2 wherein the reaction is carried out with from 1.5 to 20 moles of HF per mole of trichloromethylthiobenzoyl chloride.

5. A process as claimed in claim 1 wherein the reaction is carried out at a temperature of from 40° to 80° C.

6. A process as claimed in claim 2 wherein the reaction is carried out at a temperature of from 10° to 30° C.

* * * * *